US005674982A

United States Patent [19]

Greve et al.

[11] Patent Number: 5,674,982
[45] Date of Patent: Oct. 7, 1997

[54] MULTIMERIC FORM OF HUMAN RHINOVIRUS RECEPTOR PROTEIN

[75] Inventors: Jeffrey M. Greve, Branford; Alan McClelland, Old Saybrook, both of Conn.

[73] Assignee: Bayer Corporation, West Haven, Conn.

[21] Appl. No.: 469,588

[22] Filed: Jun. 5, 1995

Related U.S. Application Data

[63] Continuation of Ser. No. 318,039, Oct. 4, 1994, which is a continuation of Ser. No. 159,076, Nov. 29, 1993, abandoned, which is a continuation of Ser. No. 977,589, Nov. 17, 1992, abandoned, which is a continuation of Ser. No. 556,238, Jul. 20, 1990, abandoned.

[51] Int. Cl.$^6$ ............... C07K 16/28; C07K 14/705; A61K 39/44
[52] U.S. Cl. ............... 530/388.22; 424/152.1; 424/193.1; 424/194.1; 530/391.7; 530/395
[58] Field of Search ............... 530/350, 395, 530/402, 403, 388.22, 391.7; 424/185.1, 193.1, 193.4, 194.1, 152.1

[56] References Cited

U.S. PATENT DOCUMENTS

| | | | |
|---|---|---|---|
| 4,171,365 | 10/1979 | Diana et al. | 424/273 |
| 4,209,526 | 6/1980 | Diana et al. | 424/273 |
| 4,232,161 | 11/1980 | Diana et al. | 546/279 |
| 4,234,725 | 11/1980 | Diana et al. | 544/140 |
| 4,261,928 | 4/1981 | Diana et al. | 568/331 |
| 4,372,976 | 2/1983 | Diana | 424/331 |
| 4,427,653 | 1/1984 | Springer | 424/85 |
| 4,451,476 | 5/1984 | Diana | 424/272 |
| 4,843,087 | 6/1989 | Diana | 514/374 |
| 4,956,281 | 9/1990 | Wallner et al. | 435/69.3 |
| 5,109,123 | 4/1992 | Reinherz et al. | 536/27 |
| 5,235,049 | 8/1993 | McClelland et al. | 435/240.2 |
| 5,284,931 | 2/1994 | Springer et al. | 424/85.8 |

FOREIGN PATENT DOCUMENTS

| | | | |
|---|---|---|---|
| A-14630/88 | 10/1988 | Australia | C07K 15/12 |
| B-48767/90 | 2/1990 | Australia | C07K 13/00 |
| 0169146A3 | 1/1986 | European Pat. Off. | C12N 15/00 |
| 0169729A2 | 1/1986 | European Pat. Off. | G01N 33/577 |
| 0192175A2 | 8/1986 | European Pat. Off. | C12N 5/00 |
| 0207453A2 | 1/1987 | European Pat. Off. | C07D 413/12 |
| 02276004A2 | 7/1987 | European Pat. Off. | C07K 7/08 |
| 0261403A2 | 3/1988 | European Pat. Off. | C12N 15/00 |
| 0280578A2 | 8/1988 | European Pat. Off. | C07K 3/20 |
| 0287076B1 | 10/1988 | European Pat. Off. | C12P 21/00 |
| 0289949A2 | 11/1988 | European Pat. Off. | C12N 15/00 |
| 0314863A2 | 5/1989 | European Pat. Off. | A61K 37/02 |
| 0319815A2 | 6/1989 | European Pat. Off. | C12N 5/00 |
| 0380068A1 | 1/1990 | European Pat. Off. | C12N 15/85 |
| 0362526A2 | 4/1990 | European Pat. Off. | C12N 15/12 |
| 0362531A1 | 4/1990 | European Pat. Off. | C07K 13/00 |
| 0364690A2 | 4/1990 | European Pat. Off. | C07K 15/00 |
| 0365837A2 | 5/1990 | European Pat. Off. | A61K 37/02 |
| 03799004A1 | 8/1990 | European Pat. Off. | C07K 13/00 |
| 0387668A1 | 9/1990 | European Pat. Off. | C12N 15/12 |
| 0387701B1 | 9/1990 | European Pat. Off. | A61K 37/02 |
| 0391088A2 | 10/1990 | European Pat. Off. | A61K 37/02 |
| 0459577A2 | 12/1991 | European Pat. Off. | C07K 15/28 |
| 3712678A1 | 10/1988 | Germany | C12N 5/00 |
| 90/0469 | 10/1990 | Saudi Arabia | |
| 2022826 | 12/1979 | United Kingdom | G01N 33/16 |
| WO 88/06592 | 9/1988 | WIPO | C07H 21/04 |
| WO 89/10938 | 11/1989 | WIPO | C07K 9/00 |
| WO 90/03400 | 4/1990 | WIPO | C07K 15/14 |
| WO 90/10646 | 9/1990 | WIPO | C07K 13/00 |
| WO 90/10652 | 9/1990 | WIPO | C07K 15/14 |
| WO 90/13316 | 11/1990 | WIPO | A61K 39/395 |
| WO 91/18010 | 11/1991 | WIPO | C07K 5/06 |
| WO 91/18011 | 11/1991 | WIPO | C07K 5/08 |
| WO 91/16927 | 11/1991 | WIPO | A61K 39/395 |
| WO 91/16928 | 11/1991 | WIPO | A61K 39/395 |

OTHER PUBLICATIONS

Abraham, G. and Colonno, R. J., "Many Rhinovirus Serotypes Share the Same Cellular Receptor", J. Virol. 51:340–345 (1984).

Anasetti et al., "Activation of Natural Killer Cells by LFA-3 Binding to CD2", Publication, Fred Hutchinson Cancer Research Center, Seattle WA, and Molecular Diagnostics, West Haven, CT (U.S.A.).

Argenbright et al., "Monoclonal Antibodies to the Leukocyte Membrane CD18 Glycoprotein Complex and to Intercellular Adhesion Molecule–1 Inhibit Leukocyte–Endothelial Adhesion in Rabbits", J. Leukoc. Biol. 49:253–257 (1991).

Argenbright, L. W. and Barton, R. W., "Interactions of Leukocyte Integrins with Intercellular Adhesion Molecule–1 in the Production of Inflammatory Vascular Injury In Vivo: the Shwartzman Reaction Revisited", J. Clin. Invest. 89 (1): 259–272 (1992).

Badger et al., "Structure Analysis of a Series of Antiviral Agents Complexed with Human Rhinovirus 14", PNAS 85:3304–3308 (1988).

Bangham, C. R. M. and McMichael, A. J., "Nosing ahead in the cold war" Nature 334:16 (1990).

Bebbington, C. R., and Hentschel, C. C. G. "The use of vectors based on gene amplification for the expression of cloned genes in mammalian cells" DNA Cloning 3:163–186 (1987).

Blann, A. D., "Cell Hybrids: an important new source of antibody production" Med. Lab. Sci. 36:329–338 (1979).

Bock et al., "Characterization of soluble forms of NCAM", FEBS Lett 225(1,2):33–36 (1987).

(List continued on next page.)

Primary Examiner—Thomas M. Cunningham

[57] ABSTRACT

The present invention relates to novel forms and configurations of intercellular adhesion molecule (ICAM) including multimeric configurations that effectively bind to human rhinovirus and can effectively reduce HRV infectivity. When in a multimeric configuration, preferably as dimers, these proteins display enhanced binding of HRV and are able to reduce HRV infectivity as well as the infectivity of other viruses known to bind to the "major" group human rhinovirus receptor (HRR). The multimerized proteins may also be used to block tICAM interaction with lymphocyte function–associated antigen–1 (LFA-1).

3 Claims, No Drawings

OTHER PUBLICATIONS

Bowie et al., "Deciphering the Message in Protein Sequences: Tolerance to Amino Acid Substitutions", Science 247:1306–1310 (1990).

Campbell, B. A. and Cords, C. E., "Monoclonal Antibodies That Inhibit Attachment of Group B Coxsackieviruses", J. Virol. 48(2):561–564 (1983).

Capon et al., "Designing CD4 immunoadhesins for AIDS therapy", Nature 337:525–531 (1989).

Cate et al., "Isolation of the Bovine and Human Genes for Müllerian Inhibiting Substance and Expression of the Human Gene in Animal Cells", Cell 45:685–698 (1986).

Cole et al., "Topographic Localization of the Heparin–binding Domain of the Neural Cell Adhesion Molecule N–CAM", J. Cell Biol. 103:1739–1744 (1986).

Colonno et al., "Isolation of a Monoclonal Antibody that Blocks Attachment of the Major Group of Human Rhinoviruses", J. Virology 57:7–12 (1986).

Colonno, R. J. and Tomassini, J. E., "Viral Receptors: A Novel Approach For The Prevention Of Human Rhinovirus Infection", in *Medical Virology VI*, de la Maza, L. M. and E. M. Peterson, eds. (Elsevier, New York, 1987) 331–351.

Cooper, G.M., "Cellular Transforming Genes", Science 217: 801–806 (1982).

Couch, R.B., "Rhinoviruses", *Virology*, Second Edition, edited by B. N. Fields, D. M. Knipe et al. Raven Press, Ltd., New York, 607–629 (1990).

Couch et al., "Effect of Route Inoculation on Experimental Respiratory Viral Disease in Volunteers and Evidence for Airborne Transmission", Bacteriol. Rev. 30:517–529 (1966).

Creighton, T.E., *Proteins* by W. H. Freeman and Company, New York, 33–34 (1984).

Crump et al., "In Vitro Inhibitory Activity of Soluble ICAM–1 for the Numbered Serotypes of Human Rhinovirus", Antiviral Chemistry and Chemother. 4 (6): 323–327 (1993).

Cunningham et al., "Neural Cell Adhesion Molecule: Structure, Immunoglobulin–Like Domains, Cell Surface Modulation, and Alternative RNA Splicing", Science 236:799–806 (1987).

Cybulsky, M. I. and Gimbrone, Jr., M. A., "Endothelial Expression of a Mononuclear Leukocyte Adhesion Molecule During Atherogenesis", Science 251:788–791 (1991).

D'Alessio et al., "Short–Duration Exposure and the Transmission of Rhinoviral Colds", J. Inf. Dis. 150(2):189–193 (1984).

Deen et al., "A Soluble Form of CD4 (T4) Protein Inhibits AIDS Virus Infection", Nature 331:82–86 (1988).

Dick, E.C., "Experimental Infection of Chimpanzees with Human Rhinovirus Types 14 and 43", Proceedings Of The Society For Experimental Biology And Medicine 127:1079–1081 (1968).

Dochez et al., "Studies in the Common Cold. IV. Experimental Transmission of the Common Cold to Anthropoid Apes and Human Beings by Means of a Filtrable Agent", J. Exp. Med. 52:701–716 (1930).

Douglas et al., "Prophylactic Efficacy of Intranasal Alpha 2–Interferon Against Rhinovirus Infections in the Family Setting", The New England J. of Med. 314:65–70 (1986).

Douglas, R. G., "Pathogenesis of Rhinovirus Common Colds in Human Volunteers", Annals of Otology, Rhinology and Laryngology 79:563–571 (1970).

Dustin et al., "Induction by IL 1 and Interferon–γ: Tissue Distribution, Biochemistry, and Function of a Natural Adherence Molecule (ICAM–1)", J. Immunol. 137(1):245–254 (1986).

Dustin et al., "Supergene Families Meet in the Immune System" Immunology Today, 9 (7 and 8): 213–215 (1988).

Dustin et al., "Correlation of CD2 Binding and Functional Properties of Multimeric and Monomeric Lymphocyte Function–Associated Antigen 3", J. Exp. Med. 169:503–517 (1989).

Ey, P.L., et al., "Isolation of Pure IgG1, IgG2a, and IgG2b Immunoglobulins from Mouse Serum Using Protein A—Sepharose", Immunochemistry 15:429–436 (1978).

Fisher et al., "HIV Infection is Blocked in vitro by Recombinant Soluble CD4", Nature 331:76–78 (1988).

Fox et al., "Prevention of a Rhinovirus and Poliovirus Uncoating by WIN 51711, a New Antiviral Drug", Antimicrob. Ag. and Chemotherapy 30:110–116 (1986).

Galfrey et. al., "Antibodies to Major Histocompatibility Antigens Produced by Hybrid Cell Lines", Nature 266:550–552 (1977).

Gething, M.J. and Sambrook, J., "Construction of Influenza Haemagglutinin Genes that Code for Intracellular and Secreted Forms of the Protein" Nature 300:598–603 (1982).

Ginsberg et al., "Inhibition of Fibronectin Binding to Platelets by Proteolytic Fragments and Synthetic Peptides Which Support Fibroblast Adhesion", J. Biol. Chem. 260(7):3931–3936 (1985).

Giranda et al., "Modeling of the Human Intercellular Adhesion Molecule–1, the Human Rhinovirus Major Group Receptor" Proteins: Structure, Function, and Genetics, 7:227–233 (1990).

Gough, N., "Putting A Stop To An Immunoglobulin Message", Trends Genet. 3(9):238–240 (1987).

Gower et al., "Alternative Splicing Generates a Secreted Form of N–CAM in Muscle and Brain", Cell 55:955–964 (1988).

Graham, F.L., and Van der Eb, A. J., "A New Technique for the Assay of Infectivity of Human Adenovirus 5 DNA", Virology 52:456–467 (1973).

Green et al., "Immunogenic Structure of the Influenza Virus Hemagglutinin", Cell 28:477–487 (1982).

Greve et al., "The Major Human Rhinovirus Receptor Is ICAM–1", Cell 56:839–847 (1989).

Greve et al., "Mechanisms of Receptor–Mediated Rhinovirus Neutralization Defined by Two Soluble Forms of ICAM–1", J. Virology 65:6015–6023 (1991).

Gross–Bellard et al., "Isolation of High–Molecular–Weight DNA from Mammalian Cells", Eur. J. Biochem. 36:32–38 (1973).

Güssow, D. and Ploegh, H., "Soluble class I antigens: a conundrum with no solution?", Immunology Today 8(7, 8):220–222 (1987).

Gwaltney et al., *Diagnostic Procedures for Viral, Rickettsial and Chlamydial Infections*, N. J. Schmidt and R. W. Evans, Eds, 6th edition. p. 603, Am Pub. Health. Assoc., Washington D.C. (1989).

Halperin et al., "Exacerbations of Asthma in Adults During Experimental Rhinovirus Infection", Am. Rev. Respir. Dis. 132:976–980 (1985).

Hamparian et al., "A Collaborative Report: Rhinoviruses–Extension of the Numbering System from 89 to 100", Virology 159:191–192 (1987).

Hardy et al., "Intranasal Drug Delivery by Spray and Drops", J. Pharm. Pharmacol. 37:294–297 (1985).

Harning et al., "Serum Levels of Circulating Intercellular Adhesion Molecule 1 in Human Malignant Melanoma", Cancer Res. 51(8):5003–5005 (1991).

Hayden et al., "Safety and Efficacy of Intranasal Pirodavir (R77975) in Experimental Rhinovirus Infection", Antimicrob. Agents Chemother. 36(4):727–732 (1992).

Hayden et al., "Prevention of Natural Colds by Contact Prophylaxis with Intranasal Alpha2–Interferon", The New England Journal of Medicine, 314(2):71–75 (1986).

Hayden et al., "Modification of Experimental Rhinovirus Colds by Receptor Blockade" Antiviral Research 9:233–247 (1988).

Helenius, A. and Von Bonsdorff, C. H., "Semliki Forest Virus Membrane Proteins, Preparation and Characterization of Spike Complexes Soluble in Detergent–Free Medium" Biochimica et Biophysica Acta 436:895–899 (1976).

Hendley et al., "Relation Between Naturally acquired Immunity and Infectivity of Two Rhinoviruses in Volunteers", J. Inf. Dis. 125:243–248 (1972).

Holland, J. J. and McLaren, L. C., "The mammalian cell–virus relationship. II. Absorption, Reception and Eclipse of Poliovirus by HeLa Cells" J. Exp. Med. 109:487–504 (1959).

Holland, J. J., "Receptor affinities as Major Determinants of Enterovirus Tissue Tropisms in Humans", Virology 15:312–326.

Horton et al., "Gene Splicing by Overlap Extension: Tailor-Made Genes Using the Polyerase Chain Reaction", BioTechniques 8 (5) :528–535 (1990).

Hussey et. al., "A Soluble CD4 Protein Selectively Inhibits HIV Replication and Syncytium formation" Nature, 331:78–81 (1988).

Illum, L., "The Nasal Delivery of Peptides and Proteins", Trends in Biotech. 9:284–289 (1991).

Johnston et al., "Viruses as Precipitants of Asthma Symptoms. III. Rhinoviruses: Molecular Biology and Prospects for Future Intervention", Clin. Exp. Allergy, 23:237 (1993).

Johnston et al., "Viral Infections in Exacerbations in School Children with Cough or Wheeze: A Longitudinal Study", Am. Rev. Resp. Dis., 145:A546 (1992).

Kamarck, M. E., and Ruddle, F. H., "Somatic Cell Genetics and the Human Gene Map", Chapter 105 in *Handbook of Experimental Immunology in Four Volumes, vol. 3: Genetics and Molecular Immunology*, D. M. Weir, ed. (Blackwell Scientific Publications, Boston, MA, 1986).

Katz et al., "Chromosome Mapping of Cell Membrane Antigens Expressed on Activated B Cells", Eur. J. Immunol., 15:103–106 (1985).

Kavenoff, R., and Zimm, B. H., "Chromosome–Sized DNA Molecules from Drosophila", Chromosoma (Berl.) 41:1–27 (1973).

Kühn et al., "Gene Transfer, Expression, and Molecular Cloning of the Human Transferrin Receptor Gene", Cell 37:95–103 (1984).

Lebman et al., "A Monoclonal Antibody that Detects Expression of Transferrin Receptor in Human Erythroid Precursor Cells", Blood 59 (3):671–678 (1982).

Lemanske et al., "Rhinovirus Upper Respiratory Infection Increases Airway Hyperreactivity and Late Asthmatic Reactions", J. Clin. Invest. 83:1–10 (1989).

Littlefield, J.W., "Selection of Hybrids from Matings of Fibroblasts in vitro and Their Presumed Recombinants", Science 145:709–710 (1964).

Lonberg–Holm et al., "Unrelated Animal Viruses Share Receptors", Nature 259:679–681 (1976).

Margulies, D. H., et. al., "Engineering Soluble Major Histocompatibility Molecules: Why and How", Immunol. Res. 6:101–116 (1987).

Marlin, S.D. and Springer, T. A., "Purified Intercellular Adhesion Molecule–1 (ICAM–1) Is a Ligand for Lymphocyte Function–Associated Antigen 1 (LFA–1)", Cell 51:813–819 (1987).

Marlin et al., "A Soluble Form of Intercellular Adhesion Molecule–1 Inhibits Rhinovirus Infection", Nature 344:70–72 (1990).

Marsh et al., "Antibody–toxin Conjugation", *Immunotoxins* by Kluwer Academic Publishers, Boston, Dordrecht, Lancaster 213–237 (1988).

Marsh et al., "Interactions of Semliki Forest Virus Spike Glycoprotein Rosettes and Vesicle with Cultures Cells", J. Cell Biology 96:455–461 (1983).

McClelland et al., "Identification of Monoclonal Antibody Epitopes and Critical Residues for Rhinovirus in Domain 1 of ICAM–1", PNAS 88(18):7993–7997 (1991).

McClelland et al., "Transfectant cell lines which express the major human rhinovirus receptor, their preparation, and their uses", Chemical Abstracts 112:117175h (1990).

McCray, J. and Werner, G., "Different Rhinovirus Serotypes Neutralized by Antipeptide Antibodies", Nature 329:736–738 (1987).

Medical Microbiology: "An Introduction to Infectious Diseases", 2nd ed., J.C. Sherris, ed. (Elsevier Science Publishing Co., Inc., N.Y. 1990) pp. 514–515.

Medrano, L. and Green, H., "Picornavirus Receptors and Picornavirus Multiplication in Human–Mouse Hybrid Cell Lines", Virology 54:515–524 (1973).

Melchers et al., *Lymphocyte Hybridomas*, vol. 81 of Current Topics in Microbiology and Immunology, W. Arber, W. Henle, P.H. Hofschneider, J.H. Humphrey, J. Klein, P. Koldovsky, H. Koprowski, O. Maaloe, F. Melchers, R. Rott, H.G. Schweiger, L. Syrucek, P.K. Vogt, eds (Springer Verlang, New York, 1978).

Mendelshon et al., "Transformation of a Human Poliovirus Receptor Gene into Mouse Cells", PNAS 83:7845–7849 (1986).

Minor, P.D., "Growth, Assay and Purification of Picornaviruses", in *Virology: A Practical Approach*, B.W.J. Mahy, ed. (IRL Press Limited, Oxford, England), 25–41 (1985).

Minor et al., "Monoclonal antibodies which block cellular receptors of poliovirus", Virus Research 1:203–212 (1984).

Morein, B., "Potentiation of the Immune Response by Immunization with Antigens in Defined Multimeric Physical Forms", Veterinary Immunology and Immunopathology 17:153–159 (1987).

Niman et al., "Anti–peptide antibodies detect oncogene–related proteins in urine", PNAS 82:7924–7928 (1985).

Nobis et al., "Production of a Monoclonal Antibody against an Epitope on HeLa Cells that Is the Functional Poliovirus Binding Site", J. Gen. Virol. 66:2563–2569 (1985).

Ohlin et al., "Spectrum of Activity of Soluble Intercellular Adhesion Molecule–1 Against Rhinovirus Reference Strains and Field Isolates", Antimicrob. Agents and Chemother. 38:1413–1415 (1994).

Parham, P., "Monoclonal Antibodies Against HLA Products and Their use in Immunaffinity Purification," Methods in Enzymology 92:110–138 (1983).

Pepinsky et al., "The Increased Potency of Crossed–linked Lymphocyte Function–associated Antigen–3 (LFA–3) Multimers Is a Direct Consequence of Changes in Valency", J. Biol. Chem. 266(27):18244–18249 (1991).

Peterson, A. and Seed, B., "Genetic Analysis of Monoclonal Antibody and HIV Binding Sites on the Human Lymophocyte Antigen CD4", Cell 54:65–72 (1988).

Rossman et al., "Structure of a Human Common Cold Virus and Functiona Relationship to other Picornaviruses", Nature 317:145–153 (1985).

Rothlein et al., "A Form of Circulating ICAM–1 In Human Serum", J. Immuno. 147 (11) :3788–3793 (1991).

Rothlein et al., "A Human Intercellular Adhesion Molecule (ICAM–1) Distinct From LFA–1", J. Immuno. 137 (4):1270–1274 (1986).

Ruddle et al., "DNA–Mediated Gene Transfer in Mammalian Gene Cloning", Genetic Engineering 6:319–338 (1984).

Ruoslahti et al., "Synthetic Peptides in the Analysis of Cell Adhesion," in *Synthetic Peptides in Biology and Medicine* Elsvier Science Publishers, pp. 191–197 (1985).

Saiki et al., "Enzymatic Amplification of β–Globin Genomic Sewuences and Restriction Site Analysis for Diagnosis of Sickle Cell Anemia," Science 230:1350–1354 (1985).

Sambrook et al., *Molecular Cloning: A Laboratory Manual*, 2d ed. (Cold Spring Harbor Laboratory Press, Cold Spring Harbor, NY. 1989) pp. 1.21–1.52.

Schipper et al., "The Nasal Mucocilliary Clearance: Relevance to Nasal Drug Delivery", Pharm. Res. 8:807–814 (1991).

Scopes, R.K., "Separation By Precipitation," in *Protein Purification: Principles & Practice* (1982) Springler Verlag, NY, pp. 39–46.

Seed, B. and Aruffo, A., "Molecular Cloning of the CD2 antigen, the T–Cell Erythrocyte Receptor, by a Rapid Immunoselection Procedure," PNAS 84:3365–3369 (1987).

Seed, B., "An LFA–3 cDNA Encodes a Phospholipid–Linked Membrane Protein Homologous to its Receptor CD2," Nature 329:840–842 (1987).

Seth et al., "Circulating ICAM–1 isoforms: Diagnostic Prospects for Inflammatory and Immune Disorders," Lancet 338:83–84 (1991).

Sherman–Gold, R., "Companies Pursue Therapies Based on Complex Cell Adhesion Molecules", Genetic Engineering News pp. 6–7,14 (Jul. 1993).

Sherry, B. and Rueckert, R., "Evidence for at Least Two Dominant Neutralization Antigens on Human Rhinovirus 14," J. Virol. 53(1):137–143 (1985).

Shih, C. and Weinberg, R. A., "Isolation of a Transforming Sequence from a Human Bladder Carcinoma Cell Line," Cell 29:161–169 (1982).

Shipkowitz et al., "Antiviral Activity of a bis–Benzimidazole Against Esperimental Rhinovirus Infections in Chimpanzees", App. Microbiol. 23(1):117–122 (1972).

Siddique et al., "The Poliovirus Sensitivity (PVS) Gene Is on Chromosome 19q12–>q13.2", Genomics 3:156–160 (1988).

Simmons et al., "ICAM, an Adhesion Ligand of LFA–1, is Homologous to the Neural Cell Adhesion Molecule NCAM," Nature 331:624–627 (1988).

Simons et al., "Formation of Protein Micelles from Amphiphilic Membrane Proteins", PNAS 75 (11):5306–5310 (1978).

Skerra, A. and Pluckthun, A., "Assembly of a Functional Immunoglobulin FV Fragment in *Escherichia Coli*", Science, 240:1038–1041 (1988).

Smith, T.J., et al., "The Site of Attachment in Human Rhinovirus 14 for 4 Antiviral Agents that Inhibit Uncoating", Science 233:1286–1293 (1986).

Smith et al., "Blocking of HIV–1 Infectivity by a Soluble, Secreted Form of the CD4 Antigen," Science 238:1704–1707 (1987).

Smith et al., "Modification and Secretion of Human Interleukin 2 Produced in Insect Cells by a Baculovirus Expression Vector", PNAS 82:8404–8408 (1985).

Springer, T.A., "Adhesion Receptors of the Immune System", Nature 346:425–434 (1990).

Staunton et al., "Primary Structure of ICAM–1 Demonstrates Interaction between Members of the Immunoglobulin and Integrin Supergene Families," Cell 52:925–933 (1988).

Staunton et al., "The Arrangement of the Immunoglobulin–Like Domains of ICAM–1 and the Binding Sites for LFA–1 and Rhinovirus," Cell 61:243–254 (1990).

Staunton et al., "A Cell Adhesion Molecule, ICAM–1, is the Major Surface Receptor for Rhinoviruses," Cell 56:849–853 (1989).

Steis et al., "Serum Soluble IL–2 Receptor as a Tumor Marker in Patients with Hairy Cell Leukemia", Blood 71 (5):1304–1309 (May 1988).

Sundquist et al., "Influenza Virus ISCOMs: Antibody Response in Anaimals", Vaccine 6:49–53 (1988).

Sundquist et al., "Influenza Virus ISCOMs: Biochemical Characterization", Vaccine 6:44–48 (1988).

Tomassini, J.E., "Isolation, Characterization and Cloning of the Cellular Receptor for the Major Group of Human Rhinoviruses," Ph.D. Thesis, University of Pennsylvania (1986).

Tomassini, J.E. and Colonno, R. J., "Isolation of a Receptor Protein Involved in Attachment of Human Rhinoviruses," J. Virol. 58(2):290–295 (1986).

Tomassini et al., "CDNA Cloning Reveals that the Major Group Rhinovirus Receptor on HeLa Cells is Intercellular Adhesion Molecule 1," PNAS 86 :4907–4911 (1989).

Towbin et al., "Electrophoretic Transfer of Proteins from Polyacrylamide Gels to Nitrocellulose Sheets: Procedure and Some Applications", PNAS 76 (9):4350–4354 (1979).

Traunecker et al., "Highly Efficient Neutralization of HIV with Recombinant CD4–Immunoglobulin Molecules," Nature 399: 68–70 (1989).

Traunecker et al., "Soluble CD4 Molecules Neutralize Human Immunodeficiency Virus Type 1" Nature 331: 84–86 (1988).

Turner at el., "Efficacy of Oral WIN 54954 for Prophylaxis of Experimental Rhinovirus Infection", 37: 297–300 (1993).

Urlaub, G. and Chasin, L. A., "Isolation of Chinese Hamster Cell Mutants Deficient in Dihydrofolate Reductase Activity," PNAS USA 77 (7):4216–4220 (1980).

Wade, N., "Hybridomas: A Protent New Biotechnology," Science 208:692–693 (1980).

Welsh, K.I. "Antibody Production Made Easier," Nature 266: 495 (1977).

Wigler et al., "Transformation of Mammalian Cells with Genes from Procaryotes and Eucaryotes," Cell 16:777–785 (1979).

Williams, A. F., "A Year in the Life of the Immunoglobulin Superfamily", Immunology Today 8(10):298–303 (1987).

Williams, A. F. and Barclay, A. N., "The Immunoglobulin Superfamily–Domains for Cell Surface Recognition[1,2]", Ann. Rev. Immunol. 6:381–405 (1988).

Winther et al., "Sites of Rhinovirus Recovery After Point Inoculation of the Upper Airway", JAMA 256(13):1763–1767 (1986).

Woods et al., "In Vitro and In Vivo Activities of WIN 54954, a New Broad Spectrum Antipicornavirus Drug", Antimicrob. Agents Chemother 33:2069–2074 (1989).

Zettlmeissl et al., "Expression and Characterization of Human CD4: Immunoglobulin Fusion Proteins," DNA and Cell Biology 9:347–353 (1990).

Braude, A. (ed.s), "Infectious Diseases and Medical Microbiology, 2nd edition, W.B. Saunders Co., Philadelphia, PA, (1986) chapter 65 Picornaviruses", pp. 521–529.

Gennaro, A.R. (ed.), Remington's Pharmaceutical Sciences, 18th edition, Mack Publishing Co., Easton, PA (1990), "Drug Absorption, Action and Disposition", pp. 707–721.

Martin et al., "Efficient Neutralization and Disruption of Rhinovirus by Chimeric ICAM–1/Immunoglobulin Molecules", J. Virology, 67(6):3561–3568 (Jun. 1993).

Hendley et al., "Transmission of Rhinovirus Colds By Self–Inoculation", The New England Journal of Medicine, 288(26):1361–1364 (Jun. 28, 1973).

Hendley, J. O., and Gwaltney, J. M., Jr., "Mechanisms of Transmission of Rhinovirus Infections", Epidemiologic Reviews, 10:242–257 (1988).

Suter, David, Associated Press, "Tests for a Nasal Spray to Deflect Cold Viruses", New York Times, Sep. 20, 1995.

Manning, Anita, "War on Bacteria Mix of Victories Amid Warnings", USA Today, Sep. 20, 1995.

Haney, Daniel Q., "Beyond Chicken Soup. Nasal Spray Keeps Chimps From Catching Cold Virus", St. Louis Post Dispatch, Sep. 20, 1995.

Associated Press, "Common Colds: Nasal Spray May Help Keep The Sniffles Away", Atlanta Constitution, Sep. 20, 1995.

Associated Press, "Drug Sprays Away Colds", New York Post, Sep. 20, 1995.

Haney, Daniel Q., Associated Press, "The Cold War: Scientists Develop Spray That May End Sniffles", Arizona Republic, Sep. 20, 1995.

Haney, Daniel Q., Associated Press, "For Colds, Nasal Spray Holds Hope. A Protein Swamps The Virus With Potential Targets In The Nose. Its a Decoy Trick", Philadelphia Inquirer, Sep. 20, 1995.

Associated Press, "Simple Nasal Spray May Be Able To Keep Common Cold Away. Medicine Successful On Chimps So Far", Washington Times, Sep. 20, 1995.

Associated Press, "Doctors Sniffing Out Spray to Fight Colds", Denver Post, Sep. 20, 1995.

Associated Press, "Someday Soon, A Simple Sniff Should Snuff The Sniffles", Houston Chronicle, Sep. 20, 1995.

Haney, Daniel Q., Associated Press, "Spray May Ward Off Sniffles. Nasal Treatment Studied To Keep Cold Viruses From Invading Victim", Denver–Rocky Mountain News, Sep. 20, 1995.

Haney, Daniel Q., Associated Press, "Scientists Make Headway In Cold War With Nose Spray", Chicago Sun–Times, Sep. 20, 1995.

Haney, Daniel Q., Associated Press, "Labs Busy Working On Nose Spray To Keep Colds Away", Charlotte Observer, Sep. 20, 1995.

Associated Press, "Nasal Spray May Prevent Sniffles", Miami Herald, Sep. 20, 1995.

Associated Press, "Cure For The Cold? No, But Prevention May Be Spray Away", San Diego Union–Tribune, Sep. 20, 1995.

Haney, Daniel Q., "Nasal Spray Touted As Next–Best Thing To Cure For Colds", The Montreal Gazette, Sep. 20, 1995.

Associated Press, "Scientists Feel They Can Develop Spray To Keep The Sniffles Away", The Spectator, Sep. 20, 1995.

Haney, Daniel Q., Associated Press, "New Nasal Spray May Take Sniffles Out Of Common Cold", Cleveland Plain Dealer, Sep. 20, 1995.

Associated Press, "No Cure, But Nothing To Sniff (le) At. Nasal Spray To Block Common Cold In The Works", Minneapolis Star Tribune, Sep. 20, 1995.

Haney, Daniel Q., Associated Press, "Out Front: Progress On Cold Front. Spray May Ward Off Sniffles. Medicine Is Frist To Block Infection", Sep. 19, 1995.

Monitoring Report, "Cure For Colds Sep. 18 to Sep. 20", Video Monitoring Services of America, a Burrelle's Affiliate, New York, New York, pp. 1–3, Sep. 20, 1995.

MULTIMERIC FORM OF HUMAN RHINOVIRUS RECEPTOR PROTEIN

This is a continuation of copending application U.S. Ser. No. 08/318,039, filed 4 Oct. 1994, which is a continuation of U.S. Ser. No. 08/159,076, filed 29 Nov. 1993, abandoned, which is a continuation of U.S. Ser. No. 07/977,589, filed 17 Nov. 1992, abandoned, which is a continuation of U.S. Ser. No. 07/556,238, filed 20 Jul. 1990, abandoned.

BACKGROUND OF THE INVENTION

The present invention relates to novel multimeric configurations and forms of intercellular adhesion molecule (ICAM), including both full length and truncated forms of these proteins, that effectively bind to human rhinovirus and can effectively reduce HRV infectivity.

Full length ICAM, also known as human rhinovirus receptor (HRR), is termed transmembrane ICAM (tmICAM-1) non-transmembrane ICAM forms, also known as truncated ICAM (tICAM), are less than full length. When in a multimeric configuration, preferably as dimers, these proteins display enhanced binding of human rhinovirus (HRV) and are able to reduce HRV infectivity. In addition, these multimerized proteins may also be used to reduce infectivity of other viruses that are known to bind to the 'major' group human rhinovirus receptor (HRR), such as coxsackie A virus, and may also be used to block transmembrane intracellular adhesion molecule (tmICAM) interaction with lymphocyte function-associated antigen-1 (LFA-1) critical to many cell adhesion processes involved in the immunological response. Lastly, these multimerized proteins may be used to study the ICAM-1/HRV interaction especially with respect to designing other drugs directed at affecting this interaction.

Human rhinoviruses are the major causative agent of the common cold. They belong to the picornavirus family and can be classified based on the host cell receptor to which they bind. Tomassini, et al., *J. Virol.*, 58:290 (1986) reported the isolation of a receptor protein involved in the cell attachment of human rhinovirus. Approximately 90% of the more than 115 serotypes of rhinoviruses, as well as several types of coxsackie A virus, bind to a single common receptor termed the "major" human rhinovirus receptor (HRR) the remaining 10% bind to one or more other cell receptors.

Recently, Greve, J. et al., *Cell*, 56:839 (1989), co-authored by the co-inventors herein, identified the major HRR as a glycoprotein with an apparent molecular mass of 95,000 daltons and having an amino acid sequence essentially identical to that deduced from the nucleotide sequence of a previously described cell surface protein named intercellular adhesion molecule (ICAM-1). Simmons, D. et al., *Nature*, 331:624 (1988). Staunton, et al., *Cell*, 52:925–933 (1988). Subsequently, Staunton, D. E., et al., *Cell*, 56:849 (1989), confirmed that ICAM-1 is the major surface receptor for HRV. See also, Staunton, et al., *Cell*, 61:243–254 (1990).

ICAM-1 is an integral membrane protein 505 amino acids long and has: i) five immunoglobulin-like extracellular domains at the amino-terminal end (amino acid residues 1–453), ii) a hydrophobic transmembrane domain (454–477), and iii) a short cytoplasmic domain at the carboxy-terminal end (478–505). ICAM-1 is a member of the immunoglobulin supergene family and functions as a ligand for the leukocyte molecule, lymphocyte function associated molecule-1 (LFA-1), a member of the integrin family. Heterotypic binding of LFA-1 to ICAM-1 mediates cellular adhesion of diverse cell types and is important in a broad range of immune interactions induction of ICAM-1 expression by cytokines during the inflammatory response may regulate leukocyte localization to inflammatory sites. The primary structure of ICAM-1 has been found to be homologous to two cellular adhesion molecules, i.e., neural cell adhesion molecule (NCAM) and mylein-associated glycoprotein (MAG).

Several approaches to decreasing infectivity of viruses in general, and of rhinovirus in particular, have been pursued including: i) developing antibody to the cell surface receptor for use in blocking viral binding to the cell, ii) using interferon to promote an anti-viral state in host cells iii) developing various agents to inhibit viral replication iv) developing antibodies to viral capsid proteins/peptides and v) blocking viral infection with isolated cell surface receptor protein, that specifically blocks the viral binding domain of the cell surface receptor.

Using this latter approach, Greve, et al., *Cell*, 56:879 (1989), supra, reported that purified tmICAM-1 could bind to rhinovirus HRV3 in vitro. Unpublished results with HRV2, HRV3, and HRV14 demonstrate a positive correlation between the ability to bind to rhinovirus and the ability to neutralize rhinovirus particularly if the binding studies are carried out under conditions where ICAM-1 is presented in a particular form a configuration as discussed further, infra. Results (unpublished) using HRV14 and HRV2 demonstrate a positive correlation between the receptor class of the virus and the ability to bind to tmICAM-1 n vitro. That is, ICAM-1, being the major receptor, can bind to HRV3, HRV4, and other "major" receptor serotypes and neutralize them, while it does not bind or neutralize HRV2, a "minor" receptor serotype. Further studies (unpublished), using purified tmICAM-1, demonstrate that it effectively inhibits rhinovirus infectivity in a plaque-reduction assay when the rhinovirus is pretreated with tmICAM-1 (50% reduction of titer at 10 nM receptor and one log reduction of titer at 100 nM receptor protein). These data were consistent with the affinity of rhinovirus for ICAM-1 of Hela cells, which had an apparent dissociation constant of 10 nM, and indicated a direct relationship between the ability of the receptor to bind to the virus and to neutralize the virus.

Because large-scale production of tmICAM-1 is not presently economically feasible, and because maintenance of tmICAM-1 in an active form requires the use of detergents, alternate means of producing a receptor protein for use as a rhinovirus inhibitor are desirable. Forms of the tmICAM-1 cDNA gene have been developed (as well as cell lines that produce the expression products; U.S. Ser. No. 390,662) that have been genetically altered to produce truncated ICAM-1 molecules. These truncated forms of ICAM-1 (tICAM(453) and tICAM(185)) lack the transmembrane region and are secreted into the cell culture medium. They bind to rhinovirus in the assay described in Greve, et al., *Cell*, 56:879 (1989), supra, although at substantially reduced levels relative to tmICAM-1. Thus, their effectiveness as inhibitors of rhinoviral infectivity appeared to be less than that of tmICAM-1. See generally co-pending applications, U.S. Ser. No. 130,378; U.S. Ser. No. 239,570; U.S. Ser. No. 262,428; U.S. Ser. No. 239,571; and U.S. Ser. No. 390,662.

U.S. Ser. No. 239,571 filed Sep. 1, 1988 and its CIP applications U.S. Ser. No. 262,428 and U.S. Ser. No. 360, 662 are directed to the use of transmembrane rhinovirus receptor as an inhibitor of rhinovirus infectivity using nonionic detergent to maintain the transmembrane protein in solution and directed to truncated intercellular adhesion molecules (tICAM) having extracellular domains 1, 2 and 3 of transmembrane intercellular adhesion molecules (tmICAM) and which truncated forms do not require the presence of non-ionic detergent for solubilization;

U.S. Ser. No. 130,378 filed Dec. 8, 1987 and its CIP application U.S. Ser. No. 262,570 are directed to transferred cell lines which express the major rhinovirur receptor (HRR) and to the indentification of HRR as intercellular adhesion molecule; and U.S. Ser. No. 301,192 filed Jan. 24, 1989 and its CIP application U.S. Ser. No. 449,356 are directed to a naturally occurring soluble ICAM. (sICAM) related to but distinct from tmICAM in that this sICAM lacks the amino acids spanning the transmembrane region and the cytoplasmic region; in addition this sICAM has a novel sequence of 11 amino acids at the C-terminus.

Subsequently, Marlin, S. D., et al., *Nature*, 344:70 (1990), reported the construction and purification of a truncated soluble form of the normally membrane bound ICAM-1 molecule which they termed sICAM-1. It has both the transmembrane domain and the cytoplasmic domain of the protein deleted and differs from the wild-type amino acid sequence by a single conservative substitution at its carboxyl end. It is composed of residues 1–452 of ICAM-1 and of a novel phenylalanine residue at the C-terminus. These workers demonstrated that sICAM-1 was required at levels >50 µg/ml to prevent the binding of HRV14 virus to cells. However, they also found that siCAM-1 at 1 µg/ml (18 nM), when continually present in the culture medium, was able to inhibit by 50% the progression of an infection by HRV4. The inhibitory activity was correlated with the receptor class of the virus, in that coxsackie A13 but not poliovirus or HRV2 was inhibited; infectivity data for HRV14 was not reported, however. Thus, they did not demonstrate a direct correlation between binding and inhibition of infectivity. Further, as discussed in greater detail, infra, attempts to reproduce the results obtained by Marlin, et al. have not been successful and have suggested that a higher concentration of the truncated form of ICAM (10-fold higher than transmembrane ICAM) is required to produce a 50% reduction in viral titer.

To date, no one has been able to demonstrate an agent that binds to and effectively reduces infectivity of human rhinovirus (by blocking viral infection with isolated cell surface receptor protein) as effectively as tmICAM-1; accordingly there continues to exist a need in the art for a form of ICAM-1 that can effectively bind to human rhinovirus and can effectively reduce HRV infectivity.

BRIEF SUMMARY OF THE INVENTION

Provided by the invention are multimeric configurations of transmembrane ICAM (tmICAM-1) as well as multimeric configurations of non-transmembrane ICAM (tICAM). Non-transmembrane ICAM is also known as truncated ICAM, i.e, ICAM substantially without the carboxyl intracellular domain and without the hydrophobic membrane domain and includes but is not limited to the forms of tICAM(453) and tICAM(185). Non-transmembrane forms of ICAM can include functional derivatives of ICAM and mutein forms of tICAM to facilitate coupling. When the truncated ICAM forms are in a multimeric configuration, preferably as dimers, they display enhanced binding of human rhinovirus and are able to reduce viral infectivity. The different forms of ICAM, transmembrane and non-transmembrane, can be multimerized by adsorption to a support. This support can be made of materials such as nitrocellulose, PVDF, DEAE, lipid polymers, as well as amino dextran, or a variety of inert polymers that can adsorb or can be coupled to tICAM, either with or without a spacer or linker.

Multimeric ICAM can also be multimerized by coupling the ICAM to for example, an antibody, a protein carrier, or a cross-linking reagent. An example of an antibody includes anti-ICAM antibody, CL 203; suitable protein carriers include albumin and proteoglycans; and suitable cross-linking reagents include heterobifunctional and homobifunctional cross-linking reagents such as bifunctional N-hydroxysuccinimide esters, imidoesters, or bis-maleimidohexanes. To facilitate coupling, the ICAM can be modified at either the carboxyl end or the the amino end with a reactive amino acid residue such as lysine, cysteine, or other amino acid residue(s) that provide a site(s) to facilitate coupling. These types of modified ICAM are referred to as muteins. In addition, the ICAM can be modified at either termini to comprise a lipid capable of promoting formation of oligomer micelles. The ICAM comprising the multimeric ICAM can be either fully glycosylated, partially glycosylated, or non-glycosylated.

Also provided by the invention are methods for enhancing binding of ICAM and functional derivatives thereof to a ligand, i.e., human rhinovirus, and "major" group receptor viruses, lymphocyte function-associated antigen-1 (LFA-1), plasmodium falciparum (malaria) and the like, wherein the ICAM is presented in a form and a configuration to the ligand and wherein the binding of the ICAM to the ligand is enhanced. The ICAM form can either be transmembrane or non-transmembrane (truncated). Truncated ICAM is ICAM substantially without the carboxyl intracellular domain and without the hydrophobic membrane domain. Preferred truncated forms of ICAM include tICAM(453) and tICAM (185). The ICAM can be modified at either the carboxyl terminus or the amino terminus to enhance multimeric ICAM formation. These modifications can include the addition of reactive amino acid residues such as lysine, cysteine, or other amino acid residue(s) that provide a site(s) to facilitate coupling. The nucleotide sequence for the ICAM of the method can be contained in a vector, such as a plasmid, and the vector can be introduced into a host cell, for example eukaryotic or prokaryotic cells. The preferred eukaryotic cell is a mammalian cell, i.e., Chinese Hamster Ovary cells; the preferred prokaryotic cell is *E. coli*.

The preferred configuration of the ICAM of the method is multimeric, dimeric being most preferred. The multimeric configuration can comprise a first ICAM cross-linked to a second ICAM or can comprise ICAM adsorbed to a support to thereby generate a multimeric configuration. The support can be high molecular weight and substantially inert polymers such as nitrocellulose, PVDF, DEAE, lipid polymers, and amino-dextran, or a variety of polymers that can adsorb and can be coupled to ICAM, either with or without a spacer or linker. The multimeric ICAM can be multimerized by coupling to for example, an antibody, a protein carrier, or a cross-linking reagent. Preferred cross-linking reagents include heterobifunctional and homobifunctional cross-linking reagents such as bifunctional N-hydroxysuccinimide esters, imidoesters, a bis-maleimidohexanes preferred protein carriers include albumin and proteoglycans; an example of a preferred antibody includes CL 203 and any other antibodies that do not interfere with HRV binding.

Also provided by the invention are novel pharmaceutical compositions comprising a pharmaceutically acceptable solvent, diluent, adjuvant or carrier, and as the active ingredient, an effective amount of a polypeptide characterized by having human rhinovirus binding activity and reduction of virus infectivity.

Other aspects and advantages of the present invention will be apparent upon consideration of the following detailed description thereof which includes numerous illustrative examples of the practice of the invention.

DETAILED DESCRIPTION

As noted, supra, tmICAM-1 isolated from mammalian cells has the capacity to neutralize human rhinoviruses belonging to the major receptor group, but only if maintained in solution with detergent. Certain soluble fragments of ICAM-1 have been found to have a reduced capacity for binding virus and do not reduce infectivity as effectively as tmICAM-1. To date, no one has been able to ascertain the reason for this reduced capacity.

It has been proposed by others that the rhinovirus receptor exists on cells in a pentameric form. Tomassini, J., and Colonno, R., *J. Virol.*, 58:290–295 (1986). However, quantitation (unpublished results of the co-inventors herein) of the rhinovirus and anti-ICAM-1 monoclonal antibody binding to Hela cells has revealed a maximum of 30,000 virions bound per cell (determined by the binding of $^{35}S$ methionine-labeled HRV) and 50,000–60,000 ICAM-1 molecules per cell (determined by the binding of radio-labeled Mab to ICAM-1). These results prompted further studies to examine the possibility that rather than five, only between 1 and 2 ICAM-1 molecules on the surface of cells are bound per HRV particle bound to the cell.

Genetically engineered forms of truncated ICAM-1 that lack the C-terminal transmembrane domain and that are secreted into the culture medium of mammalian cells transferred with the recombinant gene. The purification of two of these secreted ICAM molecules, tICAM(453) and tICAM (185), from spent culture medium or cells stably transfected with the genes therefor, is described below. In a solution-HRV binding assay and in an HRV neutralization assay, it was found that tICAM(453) has substantially reduced (approximately 200-fold) avidity for HRV relative to tmICAM-1. However, when either tmICAM-1 or tICAM (453) or tICAM(185) is first adsorbed to any one of a number of insoluble supports, such as nitrocellulose, PVDF (polyvinylidene difluoride), or DEAE (diethylaminoethyl) membranes, and then incubated with radioactive HRV, the virus-binding activity of tICAM(453) becomes comparable to that of tmICAM-1. This binding of multimeric tICAM (453) or of multimeric tICAM(185) to HRV has the same properties as the binding of HRV to ICAM-1 on Hela cells: it is inhibited by anti-ICAM-1 Mabs, it is specific for rhinoviruses of the major receptor group, and has the same temperature dependence as the binding of rhinovirus to cells (i.e., binds well at 37° C. and undetectably at 4° C.).

As used herein, the following abbreviations and terms include, but are not necessarily limited to, the following definitions.

| Abbreviation | Definition |
|---|---|
| ICAM | Intercellular adhesion molecule - may be used to denote both full length (transmembrane) and truncated (non-transmembrane) forms of the protein. |
| ICAM-1 | Intercellular adhesion molecule-1, also known as ICAM, tmICAM-1; denoting the full length transmembrane protein |
| tmICAM-1 | Transmembrane intercellular adhesion molecule-1, also known as human rhinovirus receptor (HRR)-requires e.g., detergent conditions to be solubilized. |
| sICAM-1 | A naturally occurring soluble ICAM-1 having both the transmembrane and the cytoplasmic domain of ICAM-1 deleted; amino acids 1–442 plus 11 novel amino acids; distinguishable from Staunton, et al. tICAM453 which consists of amino acids 1–453 with the terminal tyrosine replaced with phenylalanine. |
| tICAM | Truncated intracellular adhesion molecule, also known as non-transmembrane ICAM. |
| tICAM(453) | Truncated form of ICAM - extracellular amino terminal domain of ICAM; having the transmembrane domain and cytoplasmic domain of ICAM-1 deleted; also referred to as sICAM-1 by Marlin, et al. |
| tICAM(185) | Truncated form of ICAM - extracellular amino terminal domain of ICAM having the transmembrane domain and cytoplasmic domain of ICAM-1 deleted. |

"Multimerzation" and "multimeric" include, but are not limited to dimerization and dimeric, and include any multimeric configuration of the ICAM-1 molecule, or fragment thereof, that is effective in reducing viral binding and infectivity;

"transmembrane" generally means forms of the ICAM-1 protein molecule which possess a hydrophobic membrane-spanning sequence and which are membrane bound;

"non-transmembrane" generally means soluble forms of the ICAM-1 protein including so-called "truncated" forms of the protein that, rather than being membrane bound, are secreted into the cell culture medium as soluble proteins, as well as "transmembrane" forms that have been solubilized from cell membranes by lysing cells in non-ionic detergent;

"truncated" generally includes any protein form that is less than the full length transmembrane form of ICAM;

"form" is generally used herein to distinguish among full length and partial length ICAM forms whereas "configuration" is generally used to distinguish among monomeric, dimeric, and multimeric configurations of possible ICAM forms;

all forms and configurations off the ICAM-1 molecule whether full length or a fragment thereof, including muteins, whether monomeric or multimeric, may be fully or partially glycosylated, or completely unglycosylated, as long as the molecule remains effective in reducing viral binding and infectivity;

"ligand" is generally used herein to include anything capable of binding to at least one of any of the forms and configurations of ICAM and includes, but is not limited to, human rhinovirus, other viruses that bind to the "major" group human rhinovirus receptor, lymphocyte function-associated antigen-1, and plasmodium falciparum (malaria); and "human rhinovirus" generally includes all human serotypes of human rhinovirus as catalogued in Hamparian, V., et al., *Virol.*, 159:191–192 (1987).

The following examples illustrate practice of the invention.

Example 1 relates to growth, purification and assay of rhinoviruses;

Example 2 relates to production and isolation of monoclonal antibodies to ICAM-1;

Example 3 relates to construction of non-transmembrane truncated forms of ICAM cDNA from full length ICAM-1 cDNA;

Example 4 relates to transfection of mammalian-cells and expression of non-transmembrane truncated forms off ICAM cDNA;

Example 5 relates to isolation and purification of non-transmembrane truncated forms of ICAM-1;

Example 6 relates to radioactive labeling of tmICAM-1, tICAM(185), and tICAM(453) and demonstration of retained capacity for binding to monoclonal antibodies;

Example 7 relates to human rhinovirus binding assays of transmembrane and of transmembrane truncated forms of ICAM-1;

Example 8 relates to CL203 IgG antibody-mediated cross-linking of tICAM(453);

Example 9 relates to multimerization of transmembrane and of non-transmembrane truncated forms of ICAM-1;

Example 10 relates to infectivity-neutralization assay of multimeric transmembrane and of multimeric non-transmembrane truncated forms of ICAM-1; and Example 11 relates to use of multimeric forms of transmembrane and truncated forms of ICAM-1, as effective inhibitors of ICAM/FLA-1 interaction.

EXAMPLE 1

GROWTH, PURIFICATION AND ASSAY OF RHINOVIRUSES

Rhinoviruses were grown, purified, and assayed essentially as described in Abraham, G., et al., *J. Virol.*, 51:340 (1984) and Greve, et al., *Cell*, 56:839 (1989). The serotypes chosen for these studies include HRV14, the standard in the field, and HRV3, which has an approximately 10-fold higher affinity for ICAM than does HRV14. HRV2, which binds to the "minor" receptor rather than the "major" receptor, was used as a negative control.

Rhinoviruses HRV2, HRV3, and HRV14 were obtained from the American Type Culture Collection, plaque purified, and isolated from lysates of infected HeLa-S3 cells. Purified rhinovirus was prepared by polyethylene, glycol precipitation and sucrose gradient sedimentation. Viral purity was assessed by SDS-PAGE analysis of capsid proteins and by electron microscopy. Infectivity was quantitated by a limiting dilution infectivity assay scoring for cytophathic effect, essentially as described by Minor, P. D., Growth, assay and purification of picornaviruses, In Virology: A Practical Approach, B. W. J. Mahy, ed (Oxford: IRL Press), pp. 25–41.

EXAMPLE 2

PRODUCTION AND ISOLATION OF MONOCLONAL ANTIBODIES TO ICAM-1

BALB/cByJ female mice were immunized by intraperitoneal injection of $10^7$ intact HeLa cells-in 0.5 ml of phosphate-buffered saline (PBS) three times at 3 week intervals. Two weeks later the mice were bled and aliquots of serum were tested for protective effects against HRV14 infection of HeLa cells. Positive mice were boosted by a final injection of $10^7$ HeLa cells, and 3 days later spleen cells were fused to P3X63-Ag8.653 myeloma cells (Galfre, et al., *Nature*, 266:550–552 (1977)) to produce a total of approximately 700 hybridoma-containing wells. Each well was tested by incubating $3\times10^4$ HeLa cells in 96-well plates with 100 μl of supernatant for 1 hr at 37° C.; the cells were then washed with PBS, and a sufficient amount of HRV14 was added to give complete cytopathic effect in 24–36 hr. Wells that were positive (protected from infection) were scored at 36 hr.

Cells were removed from wells which scored positive in the first screen and cloned by limiting dilution in 96-well microtiter plates. Supernatants from these wells were tested in the cell protection assay and positive wells were again identified. Further clonings were performed until all of the hybridoma containing wells were positive indicating a clonal population had been obtained. Four cloned cell lines, and their corresponding antibodies, were obtained and were designated c78.1A, c78.2A, c78.4A, c78.5A, c92.1A and c92.5A, respectively.

C92.1A was deposited on Nov. 19, 1987 with the American Type Culture Collection, 12301 Parklawn Drive, Rockville, Md. 20852 and was designated HB 9594.

EXAMPLE 3

CONSTRUCTION OF NON-TRANSMEMBRANE TRUNCATED FORMS OF ICAM cDNA FROM FULL LENGTH ICAM-1 cDNA

A. Preparation of ICAM-1 cDNA

Randomly primed cDNA was synthesized from poly A+ RNA from HE1 cells using an Amersham™ cDNA synthesis kit under conditions recommended by the supplier. PCR amplification was performed using 100 ng of cDNA for 25 cycles using primers PCR 5.1: (ggaattcATGGCTCCCAGCAGCCCCCGGCCC) and PCR 3.1: (ggaattcTCAGGGAGGCGTGGCTTGTGTGTT). Amplification cycles consisted of 94° C. 1 min, 55° C. 2 min, and 72° C. 4 min. The product of the PCR reaction was digested with EcoR1 and cloned with EcoR1 digested phage vector λGT10 (Stratagene™). Recombinant phage clones were screened by plaque hybridization using ICAM-1 specific oligonucleotides: GAGGTGTTCTCAAACAGCTC-CAGCCCTTGGGGCCGCAGGTCCAGTTC (ICAM1) and CGCTGGCAGGACAAAGGTCTGGAGCTGG-TAGGGGGCCGAGGTGTTCT (ICAM3).

A positive clone designated λHRR4 was selected and purified. The insert was removed by EcoR1 digestion and subcloned into the EcoR1 site of Bluescript KS+. This clone was designated pHRR2. The entire insert was sequenced and found to contain the entire ICAM-1 coding sequence beginning with the initiator ATG codon and ending with the TGA stop codon as specified by the PCR ICAM-1 sequence (Simmons, et al., *Nature*, 331:624 (1988) Staunton, et al., *Cell*, 52:925–933 (1988)) by a single substitution of A 1462 for G. This same change was identified in several independent clones and thus represents a polymorphism of the ICAM-1 gene.

B. Construction of tICAM-1(453) and tICAM(185).

Modified forms of the ICAM-1 cDNA were created by PCR amplification reactions (Saiki, et al., *Science*, 230:1350–1354 (1985)) using the full length ICAM-1 cDNA clone pHRR-2 as template. The plasmid DNA was digested with EcoR1 to excise the ICAM-1 insert and treated with alkaline phosphatase to prevent re-circularization of the vector in subsequent ligation steps. Ten ng of template DNA was subjected to 10 cycles of PCR amplification using oligonucleotide primers PCR5.5 and PCR3.3 for tICAM-453 and PCR5.5 and 3.10 for tICAM-185 under the following conditions:

| Temperature (°C.) | Time (mins) |
| --- | --- |
| 94 | 1 |
| 55 | 2 |
| 72 | 1.5 |
| 71 | 4 (final extension) |

PCR5.5 has the sequence: GGAATTCAAGCTTCT-CAGCCTCGCTATGGCTCCCAGCAGCCCCCGGCCC which consists of EcoR1 and HindIII sites, 12 bp ICAM-1 5' untranslated sequence, and the first 24 bp encoding the signal peptide.

PCR3.3 has the sequence: GGAATTCCTGCAGTCACT-CATACCGGGGGGAGAGCACATT which consists of EcoR1 and Pst1 sites, a stop codon, and 24 bp complementary to the bases encoding the last 8 extracellular amino acids of ICAM-1 (residues 446–453).

PCR3.10 has the sequence: TTCTAGAGGATCCT-CAAAAGGTCTGGAGCTGGTAGGGGG which consists of Xba1 and BamH1 sites, a stop codon, and 24 bp complementary to the bases encoding residues 178–185 of ICAM-1.

The PCR reaction products were digested with EcoR1 (tICAM(453)) or EcoR1 and BamH1 (tICAM(185)) and cloned into the polylinker site of Bluescript™ SK+ (Stratagene). Clones containing the desired inserts were verified by restriction analysis and DNA. sequencing. The inserts were excised from Bluescript™ by digestion with HindIII and XbaI and inserted into the expression vector CDM8 (Seed, Nature, 239:840 (1987) at the HindIII and XbaI sites. A clone containing the tICAM(453) insert designated pHRR-8.2 and a clone containing the tICAM(185) insert designated pHRR23-13 were selected and subjected to extensive sequence analysis. This verified the existence of the desired stop codons, and the integrity of the selected regions of ICAM-1 coding sequence.

These plasmids were transfected into COS cells using the DEAE-dextran techniques and the cells were cultured 72 hr. before assay. Surface expression was monitored by FACS using indirect immunofluorescence and a monoclonal antibody specific for ICAM-1. Transient expression in COS cells and immunoprecipitation of metabolically labelled ($^3$S cysteine) cell supernatants with c78.4A Nab (monoclonal antibody) demonstrated the production of soluble ICAM-1 fragments of 45 kd and 80 kd from pHRR23-13 and pHRR8.2, respectively. The preparation of stable Chinese Hamster Ovary cell transfectants is described below in Example 4.

C. Modified Non-glycosylated Transmembrane ICAM-1 Molecules

A modified full length ICAM-1 was made by simultaneous mutagenesis of N-103, N-118, N-156 and N-173 each to Q. This removes all four N-linked glycosylation sites from the extracellular D2 domain of the ICAM-1 molecule. The resultant molecule, referred to as non-glycosylated transmembrane ICAM, was expressed on the surface of COS cells and was able to bind radio-labeled HRV3 at levels comparable to unmodified ICAM-1. This result demonstrated that glycosylation of domain 2 (the first 184 amino acids) is not required or virus binding to ICAM-1.

It is expected that non-transmembrane ICAM can be similarly modified to yield modified non-glycosylated non-transmembrane ICAM-1 molecules.

D. Construction of Genetically Engineered Forms of Non-Transmembrane (Truncated) ICAM-1 Containing Reactive Residues Suitable for Cross-Linking to Form Multimers A molecule consisting of the 453 amino acid extracellular domain of ICAM-1 with the addition of a novel lysine residue at the C-terminus was constructed by PCR modification of the pHRR-2 cDNA as described above. The primers used were PCR5.5 (described, supra) and PCR 3.19 which has the sequence: TTCTAGAGGATCCTCACTTCT-CATACCGGGGGGAGAGCACATT and consists of XbaI and BamHI sites, a stop codon, a Lys codon, and 24 bases complementary to the sequence encoding amino acid residues 446 to 453. Following cloning into the CDM8 vector, production of tICAM-453K was confirmed by transient expression in COS cells. Stable CHO cell lines were generated by co-transfection with pSV2-DHFR as described previously.

The same strategy was used to add a Lys residue to the C-terminus of tICAM(185) using PCR5.5 and PCR3.20 which has the sequence: TTCTAGAGGATCCTCACT-TAAAGGTCTGGAGCTGGTAGGGGGC and consists of XbaI and BamHI sites, a stop codon, a Lys codon, and 24 bases complementary to the sequence encoding residues 178 to 185. Transient COS cell expression confirmed the production of tICAM-185 and stable CHO cell lines were derived as described previously.

Three modified forms of tICAM(1-452) that each contain an additional Cys residue were constructed by site directed mutagenesis of the full length ICAM-1 cDNA. In each construct a stop codon was introduced by changing E-453 GAG to TAG. The C-terminus is thus Y-452 Residues N-338, T-360, and Q-387 were each separately mutated to Cys using a second site directed mutagenesis. The presence of the desired mutations were confirmed by DNA sequencing.

The residues selected for mutation to Cys were selected base on a computer generated plot of surface probability which predicts surface exposure of these regions. Also, T-360 is in close proximity to N-358 which is a site of potential N-linked glycosylation. Each of the three Cys modifications was expressed and secreted into the medium of transferred COS cells. Examination of the proteins under reducing and non-reducing conditions showed no indication of the presence of dimers. It is anticipated that cross-linking reagents reactive with sulfhydryl groups can be used to cross-link the Cys modified tICAM forms to obtain multimeric forms.

EXAMPLE 4

TRANSFECTION OF CELLS AND EXPRESSION OF NON-TRANSMEMBRANE TRUNCATED FORMS OF ICAM cDNA

A. Transfection of Eukaryotic Cells

Chinese Hamster Ovary (CHO) cells deficient in dihydrofolate reductase (DHFR) were obtained from Cutter Labs (Berkeley, Calif.). The cells were co-transfected with the plasmid pSV2 DHFR which contains the mouse dihydrofolate reductase (DHFR) gene under control of the SV40 promoter, and with tICAM-453, or tICAM-184 constructs in the CDM8 vector (Seed and Aruffo, PNAS, 84:3365–3369 (1987)).

Transfections were done using both electroporation and calcium phosphate methods. Bebbington, supra. Transferred DHFR-positive cells were selected by growth on nucleoside-free media, and pools of transfectants were cloned by limiting dilution.

Cell lines that secrete tICAM were identified by testing culture supernatants with a two-site radioimmune assay (RIA) for ICAM using Mabs c78.4A and c78.5A as follows. A monoclonal antibody against one epitope on ICAM (for example, Mab c78.4A) was adsorbed to plastic 96-well plates (Immunlon plates, Dynatech Inc.), excess binding sites on the plates blocked with bovine serum albumin (BSA), and then culture supernatants incubated with the plates. The plates were then washed and incubated with $^{125}$I-Mab (directed against a second epitope on ICAM for example, c78.5A), and, after washing, the amount of bound $^{125}$IgG determined. The concentration of tICAM was determined by comparing RIA data from unknowns against a standard curve of tm-ICAM at known concentrations. Positive clones were expanded and expression of tICAM forms was confirmed by immunoprecipitation of metabolically labeled cell supernatants with Mab 78.4A.

Cell lines CT.2A (tICAM(453)) and CD12.1A (tICAM (185)) were selected or further study and were subjected to gene amplification in methotrexate containing media as described by Bebbington, et al., supra. A clone derived from CT.2A resistant to 100 nM methotrexate and a CD12.1A clone resistant to 1 µM methotrexate were used for purification of soluble truncated ICAM-1 proteins.

B. Transfection of Prokaryotic Cells

Because glycosylation of the viral binding domain of ICAM is not required to retain viral binding (as demonstrated in Example 3C), it is anticipated that prokaryotic cells, such as *E. coli*, can be successfully transfected to produce functional proteins.

EXAMPLE 5

ISOLATION AND PURIFICATION OF NON-TRANSMEMBRANE TRUNCATE FORMS OF ICAM-1

Monoclonal antibody affinity chromatography with c78.4A-Sepharose™ has been previously described in co-pending U.S. Ser. No. 130,378 and Greve, et al., *Cell*, 56:839–847 (1989). tICAM secreted into serum-containing media required additional purification steps due to the high level of contaminating protein in the serum. Before elution from the Mab-affinity column, the column was washed with 1M NaCl to remove loosely-bound proteins. For tICAM (453), the partially purified tICAM(453) eluted from the c78.4-Sepharose™ column was dialysed into 10 mM Tris (pH 6.0), absorbed onto a mono-Q™ column (Pharmacia), and eluted with a 0–0.3M NaCl gradient. tICAM184 was further purified by gel filtration on a Superose-12™ column.

It is also recognized that non-transmembrane truncated forms of ICAM-1 may be purified using standard ion exchange methodology without using monoclonal antibody affinity chromotography.

EXAMPLE 6

RADIOACTIVE LABELING OF tmICAM-1, tICAM185, AND tICAM453 AND DEMONSTRATION OF RETAINED CAPACITY FOR BINDING TO MONOCLONAL ANTIBODIES

The epitopes reactive with monoclonal antibodies c78.4A and c78.5A are conformationally-dependent epitopes and thus can be used as analytical probes for confirming retention of the native ICAM structure. Known amounts of purified ICAM were incubated with c78.4A or c78.5A IgG-Sepharose™ and the fraction of the radioactivity bound determined. These experiments showed that the purified tmICAM-1, tICAM(185), and tICAM(453) completely retained the ability to bind to these monoclonal antibodies.

Transfectants were metabolically labeled with $^{35}$S cysteine, and cell lysates (for transmembrane ICAM) or culture supernatants (for truncated ICAM) were prepared and incubated with c78.4A IgG-Sepharose™ beads. The beads were washed and adsorbed proteins were eluted with SDS and analysed by SDS-PAGE see Greve, et al., *Cell*, 56:839–847 (1989)). It was found that the isolated proteins were quantitatively bound to the c78.4A and c78.5A Mabs.

Accordingly, the tICAM(185) and tICAM(453) both have retained native ICAM structure.

EXAMPLE 7

HUMAN RHINOVIRUS BINDING ASSAYS OF TRANSMEMBRANE. AND OF NON-TRANSMEMBRANE TRUNCATED FORMS OF ICAM-1

Described below are three binding assays used to assess binding activity of the various forms of ICAM.

A. Pelleting Assay

[$^{35}$S]cysteine-labeled tmICAM-1 or tICAM was mixed with HRV3 in 100 µl of 10 mM HEPES (pH 7.5), 150 mM NaCl, 1 mM MgCl$_2$, 1 mM CaCl$_2$, 0.1% Triton X-100. The mixture was incubated for 30 min. at 37° C., cooled on ice, layered on top of a cushion of 200 µl of 10% glycerol, 0.2M triethanolamine (pH 7.5), and centrifuged in a Beckman air-driven centrifuge at 134,000× g for 30 min. at 4° C. The top 275 µl was removed, and the pellet was analyzed by SDS-PAGE and scintillation counting. Silver-staining of SDS gels of control experiments indicated that essentially all of the HRV3 is pelleted under these conditions and essentially all of the ICAM remains in the supernatant. The results are shown in Table 1.

TABLE 1

| ICAM | % ICAM Pelleted* |
|---|---|
| tmICAM-1 | 11.6% |
| tICAM(453) | 1.0% |
| tICAM(185) | 4.3% |

These data show that both truncated forms of ICAM bind to rhinovirus, but at levels substantially reduced relative to that of tmICAM.

B. Solution Binding Assay

To obtain quantitative information on the relative affinity of tmICAM and tICAM fragments in solution, a solution competition assay was developed in which soluble tmICAM or soluble tICAM fragments were used to inhibit the binding of $^{35}$S HRV3 to previously immobilized ICAM-1 nonionic detergent (Triton X-100) was included in the buffers so that the different proteins could be compared under identical conditions. First, tmICAM-1 (isolated in the presence of 0.1% octylglucoside instead of Triton X-100) was diluted 10-fold into a Tris/NaCl buffer and allowed to adsorb to the walls of a microtiter plate (Immunlon-4, Dynatech) overnight. Nonspecific binding sites on the plate were then blocked with 10 mg/ml BSA and binding experiments performed in 0.1% Triton X-100/1 mg/ml BSA/Tris/NaCl. Approximately 20,000 cpm of $^{35}$S HRV3 were mixed with varying amounts of ICAM either tmICAM, tICAM(453) or tICAM(185), incubated or 1 hour at 37° C., and then added to wells of the microtiter plates and incubated for 3 hr at 37° C. The plates were washed and the bound radioactivity determined.

As shown in Table 2, tmICAM-1 inhibits virus binding half-maximally at low concentrations (0.008 µM) while tICAM(453) and tICAM(185) inhibit at much higher concentrations (2.8 µM and 7.9 µM, respectively; or 350 to almost 1000 old higher than tmICAM.

TABLE 2

| ICAM | IC$_{50}$* |
|---|---|
| tmICAM | 8.0 ± 3.3 nM (N = 3) |
| tICAM(453) | 2.8 ± 0.6 µM (N = 3) |
| tICAM(185) | 7.9 ± 2.8 µM (N = 3) |

*IC$_{50}$ is the concentration of soluble ICAM needed to inhibit HRV3 binding by 50%.

These data confirm and extend the earlier observations that tICAM(453) and tICAM(185) do bind to rhinovirus but with lower affinities than does tmICAM-1 and provide evidence that the virus binding site is encompassed within the two N-terminal domain (185 residues) or ICAM-1.

C. Dot-Blot Assay

An alternative method of measuring binding activity was utilized in which tmICAM-1, tICAM(453), or tICAM(185) were adsorbed to nitrocellulose filters, the non-specific binding sites on the filters blocked with 10 mg/ml bovine serum albumin (BSA), and radioactive virus or $^{125}I$ Mab to ICAM-1 incubated with the filter for 60 mins at 37° C. The filters were washed with buffer and the filters exposed to X-ray film.

The amount of radioactivity bound to the filters was determined by densitometry of the autoradiograms, and the data is expressed as HRV3 binding (in arbitrary units) normalized to the amount of ICAM bound to the blot by a parallel determination of the amount of $^{125}$Mab c78.4A or c78.5A bound to the ICAM (bound to the blot). The results are shown in Table 3.

TABLE 3

| Binding of $^{35}S$ HRV3 to Immobilized ICAM* | | |
|---|---|---|
| ICAM | tICAM(453) | ratio ICAM/tICAM453 |
| 1.2 ± 1.1 | 0.52 ± 0.45 | 2.3 |

*Average of 5 experiments. Data is expressed in arbitrary densitometric units of $^{35}S$ HRV3 binding/$^{125}I$ anti-ICAM Mab binding.

Additional studies with tICAM 185 have been initiated. Binding experiments have demonstrated equivocal results. It is anticipated that steric hinderance may play a role. The size of the virus is approximately 30 nanometers. The length of tICAM(185) is less than 10 nanometers. The use of a spacer or linker would provide better accessibility or binding.

The results from this experiment indicate that under these assay conditions tICAM(453) is capable of binding rhinovirus at levels comparable to those of tmICAM-1 when the amount of virus bound was normalized to the amount of $^{125}I$ MAb bound. Further, these results indicate that the tICAM forms are capable of binding to rhinovirus, but that the binding avidity is dependent upon the configuration o the tICAM. tmICAM-1 may be a small multimer (probably a dimer) and presentation of tICAM in a multimeric form mimics this multimeric configuration.

Evidence supporting this hypothesis comes from quantitative binding studies (unpublished), in which the ratio of the maximum number of rhinovirus particles and the maximum number of antibody molecules that can be bound to cells is approximately 1.5, as discussed supra. This is in contrast to the earlier work of Tomassini, J., et al., *J. Virol.*, 58:290 (1986), which suggested a complex of five molecules needed for binding. Their conclusion was based on an erroneous interpretation of gel filtration data that failed to take into account bound detergent molecules.

EXAMPLE 8

CL203 IgG ANTIBODY-MEDIATED CROSS-LINKING tICAM(453)

To provide additional evidence that the higher relative binding activity of tmICAM-1 is due to a multimeric form of the protein, the tICAM(453) protein was pre-incubated with CL203, a monoclonal antibody to ICAM-1 that does not inhibit virus binding to ICAM-1 and binds to a site C-terminal to residue 184 Staunton, et al., *Cell*, 56:849 (1989) and *Cell*, 61:243 (1990). Thus, the antibody can effectively "cross-link" two molecules of tICAM(453), to create "dimers" of tICAM(453), yet without blocking the virus-binding site on each of the two molecules of tICAM (453). When a mixture of CL203 IgG and tICAM(453) at a 4:1 weight ratio was tested in the competition assay, it was found that the antibody cross-linked tICAM(453) inhibited HRV3 binding at a concentration 7.4-fold lower than tICAM (453) alone consistent with the idea that tmICAM-1 binds with higher affinity to rhinovirus because it is a dimer or a small multimer.

To create alternative multimeric forms of tICAM, several further modified truncated forms of ICAM were constructed as described, supra, in Example 3. These forms can then be multimerized as described in Example 9, below.

EXAMPLE 9

MULTIMERIZATION OF TRANSMEMBRANE AND NON-TRANSMEMBRANE TRUNCATED FORMS OF ICAM-1

There are several ways that tICAM can be converted to a multimeric form having enhanced viral binding and neutralization activity over the monomeric form. For example, tICAM(453) can be coupled to an inert polymer, such as amino dextran (MW 40,000) using homobifunctional (such as N-hydroxy succinimide (NHS) esters) or heterobifunctional (such as those containing NHS-ester and photoactivatable or sulfhydryl-reactive groups) cross-linking reagents utilizing the amino group on the amino dextran and an amino or other group on the tICAM. A number of examples of appropriate cross-linking reagents can be found in the Pierce Chemical Company catalog (Rockford, Ill.).

AS tICAM is poorly reactive with NHS-ester-based compounds, a tICAM with a genetically engineered C-terminal lysine residue (see Example 3) would have improved coupling efficiency to supports with homobifunctional reagents whereas genetically engineered C-terminal cysteine residues would facilitate coupling by heterobifunctional reagents such as sulfomaleimidobenzoyl-N-hydroxysuccinimide ester (MBS).

Alternatively, soluble tICAM multimers can be created by genetically engineering reactive residues into the C-terminal end of tICAM. For example, free cysteine residues can be created in relatively hydrophilic sequences in the C-terminal region of tICAM (which would have a greater tendency to be solvent-exposed). It is anticipated that this would allow for the creation of dimers in situ; alternatively, monomers could be purified and dimers created in vitro by disulfide exchange.

Another approach requires the placement of lysine residues at similar positions and cross-linking purified protein in vitro with homobifunctional NHS-esters. Examples of such lysine residues are residues 338, 360, 387.

Crosslinking cysteine residues to each other can be accomplished by reaction of tICAM with free cysteine groups with bis-maleimidohexane (Pierce Chemical Co.) or other bis-maleimido-analogs. Cross-linking free cysteine residues on tICAM to amino groups on carrier molecules can be accomplished by reaction with m-maleimidobenzoyl-N-hydroxysuccinimide ester. Crosslinking amino groups on tICAM molecules can be accomplished with homobifunctional N-hydroxysuccinimide esters (or examples, see Pierce Chemical Co. catalog). Alternatively, the carbohydrate groups on tICAM can be oxidized to aldehydes and coupled to hydrazine-activated amino groups on a carrier molecule.

EXAMPLE 10

INFECTIVITY-NEUTRALIZATION ASSAY OF TRANSMEMBRANE AND NON-TRANSMEMBRANE TRUNCATED FORMS OF ICAM-1

Three different assays for virus infectivity have been used. These different assays take into account the differences in transmembrane ICAM and non-transmembrane solubilities.

A. Plaque-reduction Assay In the Presence of Detergent

The results of this assay indicate what the highest dilution or virus is that will still be effective in killing cells. Virus is pre-incubated with transmembrane ICAM protein in the presence of 0.1% TX100, serially diluted into culture medium, incubated for 30 min with HeLa cells at $10^6$ cells/ml, diluted 10-fold, and plated out into multiple wells of a 96-well, microtiter plate having varying dilutions of virus. 0.1% TX100 was used as positive control. After 5 days, the wells are scored as either being infected or not by the presence of cytopathic effect (CPE) and the titer expressed as plaque-forming units/ml (PFU/ml) of the original virus. This assay was described in U.S. Ser. No. 239,571 and was used to demonstrate the antiviral activity of tmICAM-1 (which required the presence of detergent to remain in solution). The concentration of ICAM protein used is the initial concentration in the pre-incubation mixture; however, the ICAM protein is not present continually during the infection in that the protein is serially diluted. While the presence of detergent is required to solubilize the tmICAM, the presence or the detergent does kill cells; thus, the need for the serial dilutions.

B. Plaque-reduction Assay in the Absence of Detergent

In this plaque-reduction assay, a more traditional assay, HeLa cells are infected with serial dilution of rhinovirus as above, but detergent is not present; thus, this assay cannot be used to assay tmICAM. In this assay the tICAM is present continually in the culture medium at the indicated concentration. tmICAM-1 (which requires the presence of detergent) cannot be assayed in this system because the addition of the required detergent would kill the HeLa cells.

C. Plaque-reduction Assay In Continual Presence of Virus and ICAM

This assay is similar to the utilized by Marlin, et al. (Nature 1990) in which a culture of HeLa cells is infected with 100 PFU of virus in the presence or absence of ICAM protein and cultured approximately 4 days until cytopathic effect (CPE) is apparent. The cultures are then scored for CPE visually. The assay conditions were the same as Marlin, supra. Scoring was done visually rather than by a staining procedure using crystal violet.

In this assay, there is no detergent present the ICAM is present continually, and this assay measures a reduction in virus replication/propagation at an arbitrary point in time.

The data from these three different assays for virus infectivity is summarized in Table 4.

proteins, even when compared in different assay systems. The differences in neutralization activity of tICAM(453) in assay (A) and assay (B) indicate that the neutralization mediated by tICAM(453) requires the continual presence of tICAM(453) in the culture medium and is reversible. That the neutralization is reversible is indicated by the lack of neutralization observed in assay (A). In contrast, the neutralization activity of tmICAM-1 is >667-fold higher than tICAM(453) and than tICAM(185) in assay (A) and could be even greater in assay (B) if it were possible to have the tmICAM-1 present continually in the culture medium in the absence of detergent.

To compare these results with those of Marlin, et al., an attempt was made to reproduce their assay conditions. As shown in Table 4, there is a good correlation between the results in assay (B) and assay (C), although the IC50% for tICAM(453) is 10-fold greater than that seen by Marlin, et al. To determine if this is due to a difference in the serotype of rhinovirus used, the assay was repeated with HRV14 and HRV54 (the serotype used by Marlin, et al). The IC50% for both of these serotypes was 0.2 µM tICAM(453), indicating that there is no difference in serotype sensitivity between HRV14, HRV54, and HRV3.

To attempt to resolve this discrepancy, the same buffers that Marlin, et al. used were used to see if they affected the infectivity of rhinovirus in assay (C). Marlin, et al. prepared their sICAM-1 protein in a buffer containing 50 mM triethanolamine (TEA)/20 mM Tris. When this buffer alone was added to control infections (1/10th volume, final concentration 5 mM TEA/2 mM Tris) of HRV3 and HRV14, virtually complete inhibition of CPE was observed. Thus, it is possible that there could be buffer effects on virus replication unrelated to the presence of any form of ICAM.

EXAMPLE 11

USE OF MULTIMERIC FORMS OF TRANSMEMBRANE AND OF TRUNCATED FORMS OF ICAM-1, AS EFFECTIVE INHIBITORS OF ICAM/FLA-1 INTERACTION

The normal function of ICAM-1 is to serve as a ligand of the leukocyte integrin LFA-1; interaction between these two molecules leads to adhesion between leukocytes and a variety of other cells. The ability of tICAM(453) to inhibit adhesion between ICAM-1 and LFA-1 on cells was examined as follows. ICAM-1 was adsorbed to microtiter plates as described in Example 7C. JY cells, which express LFA-1, adhere to ICAM-expressing cells or to ICAM-1-coated culture dishes (Staunton, et al., JCB). JY cells were preincubated in the presence or absence of tICAM(453) for 30 min at 37° C., and then added to the ICAM-1-coated plates and incubated for 60 min at 37° C. The microtiter plates were then washed and the number of cells attached to the plates were counted.

TABLE 4

| | IC50% (µM)* Assay: | | |
|---|---|---|---|
| ICAM | A | B | C |
| tmICAM-1 | 0.03 | ND | ND |
| tICAM(453) | >20 | 0.2 | 0.2 |
| tICAM(185) | >20 | ND | ND |

*IC50% is defined as the concentration of ICAM protein needed to inhibit HRV3 infectivity by 50%.

These data indicate that tmICAM-1 is significantly more active in reducing viral infectivity than the truncated ICAM

TABLE 5

| Inhibition of LFA-1/ICAM-1 interaction by soluble ICAM | |
|---|---|
| tICAM(453) (µg/ml) | % control cell binding* |
| — | 100 |
| 100 | 96 |
| 300 | 93 |
| 600 | 75 |

*Binding to ICAM-1-coated microtiter plates; 10 µg/ml anti-LFA-1 or anti-ICAM-1 MAb inhibited binding to <1%.

As can be seen in Table 5, even at high concentrations of tICAM(453) (0.6 mg/ml), minimal inhibition of JY cell binding was observed. This is probably due to the fact that the adhesion between cells is a highly cooperative process involving thousands of molecules and the affinity of tICAM (453) is low. Presentation of tICAM(453) or tICAM(185) in a multimeric configuration would increase the affinity of the tICAM for cells and could serve as an effective anti-adhesive agent in inflammatory or autoimmune diseases.

The foregoing examples describe the creation of soluble, multimeric forms of tICAM that substantially increase tICAM-1 binding and neutralizing activity.

While the present invention has been described in terms of specific methods and compositions, it is understood that variations and modifications will occur to those skilled in the art upon consideration of the present invention.

For example, it is anticipated that smaller protein fragments and peptides derived from ICAM-1 that still contain the virus-binding site would also be effective in a multimeric configuration. It is also anticipated that multimeric ICAM may be effective inhibitors of the ICAM-1/LFA-1 interaction, as the affinity between these two molecules is quite low and the cell-cell binding mediated by these two molecules is highly cooperative.

Although the preferred form and configuration is a non-transmembrane (truncated) ICAM in dimeric configuration, it is not intended to preclude other forms and configurations effective in binding virus and effective in neutralizing viral activity from being included in the scope of the present invention.

Further, it is anticipated that the general method of the invention of preparing soluble protein forms from insoluble, normally membrane bound receptor proteins can be used to prepare soluble multimeric forms of other receptor proteins useful for binding to and decreasing infectivity of viruses other than those that bind to the "major group" receptor. Such other viruses include polio, Herpes Simplex, and Epstein-Barr virus.

Numerous modifications and variations in the invention as described in the above illustrative examples are expected to occur to those skilled in the art and consequently only such limitations as appear in the appended claims should be placed thereon.

Accordingly it is intended in the appended claims to cover all such equivalent variations which come within the scope of the invention as claimed.

What is claimed is:

1. A dimeric antiviral agent comprising an antibody selected from the group consisting of CL 203 and antibodies which bind to the same epitope as CL203, said antibody being bound to two monomers wherein said monomers may be the same or different and are each independently selected from the group consisting of truncated forms of intercellular adhesions molecule-1 (tICAMs).

2. The dimeric antiviral agent according to claim 1 wherein said monomer is tICAM(453).

3. The dimeric antiviral agent according to claim 1 wherein antibody is CL203.

* * * * *